United States Patent
Glaser

(10) Patent No.: US 11,439,737 B2
(45) Date of Patent: Sep. 13, 2022

(54) DEVICE FOR EXTRACORPOREAL BLOOD TREATMENT AND METHOD FOR OPERATING AN EXTRACORPOREAL BLOOD TREATMENT DEVICE

(71) Applicant: FRESENIUS MEDICAL CARE DEUTSCHLAND GMBH, Bad Homburg (DE)

(72) Inventor: Benedict Glaser, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 469 days.

(21) Appl. No.: 16/500,822

(22) PCT Filed: Apr. 10, 2018

(86) PCT No.: PCT/EP2018/059207
§ 371 (c)(1),
(2) Date: Oct. 4, 2019

(87) PCT Pub. No.: WO2018/189207
PCT Pub. Date: Oct. 18, 2018

(65) Prior Publication Data
US 2020/0108193 A1 Apr. 9, 2020

(30) Foreign Application Priority Data
Apr. 11, 2017 (DE) .................. 10 2017 003 508.3

(51) Int. Cl.
*A61M 1/16* (2006.01)
*H05K 7/20* (2006.01)

(52) U.S. Cl.
CPC ........ *A61M 1/1656* (2013.01); *A61M 1/1686* (2013.01); *H05K 7/20254* (2013.01);
(Continued)

(58) Field of Classification Search
CPC .... A61M 1/16; A61M 1/1621; A61M 1/1656; A61M 1/1686; A61M 2205/3368;
(Continued)

(56) References Cited

U.S. PATENT DOCUMENTS

2011/0309019 A1 12/2011 Ahrens
2013/0136431 A1 5/2013 Peters et al.
(Continued)

FOREIGN PATENT DOCUMENTS

| DE | 10056172 A1 | 6/2002 |
| DE | 102010031802 A1 | 1/2012 |
| DE | 102015217281 A1 | 3/2017 |

OTHER PUBLICATIONS

International Preliminary Report on Patentability issued in corresponding International Patent Application No. PCT/EP2018/059207 dated Oct. 15, 2019 (with English translation) (8 pages).
(Continued)

*Primary Examiner* — Dirk R Bass
(74) *Attorney, Agent, or Firm* — Kilyk & Bowersox, P.L.L.C.

(57) ABSTRACT

The invention relates to a device for extracorporeal blood treatment, having a hydraulic system B which comprises multiple lines (7), (9) for providing dialysate for a dialyser (3) and having a control system (15) which comprises multiple electrical components (17A), (17B), (17C). The invention also relates to a method for operating a device for extracorporeal blood treatment which has a hydraulic system which comprises multiple lines for providing dialysate for a dialyser and a control system which comprises multiple electrical components, wherein the dialysate is produced using a liquid supplied to the device for extracorporeal blood treatment. The extracorporeal blood treatment device is a blood treatment device which has a central connection (11) to allow a liquid, in particular permeate (pure water), to be supplied to the machine. The blood treatment device is characterised by a cooling apparatus (19) for cooling at least one of the electrical components (17A), (17B), (17C) of the control system (15), said cooling apparatus using the liquid, in particular permeate (pure water), supplied centrally to the
(Continued)

Figure 1:
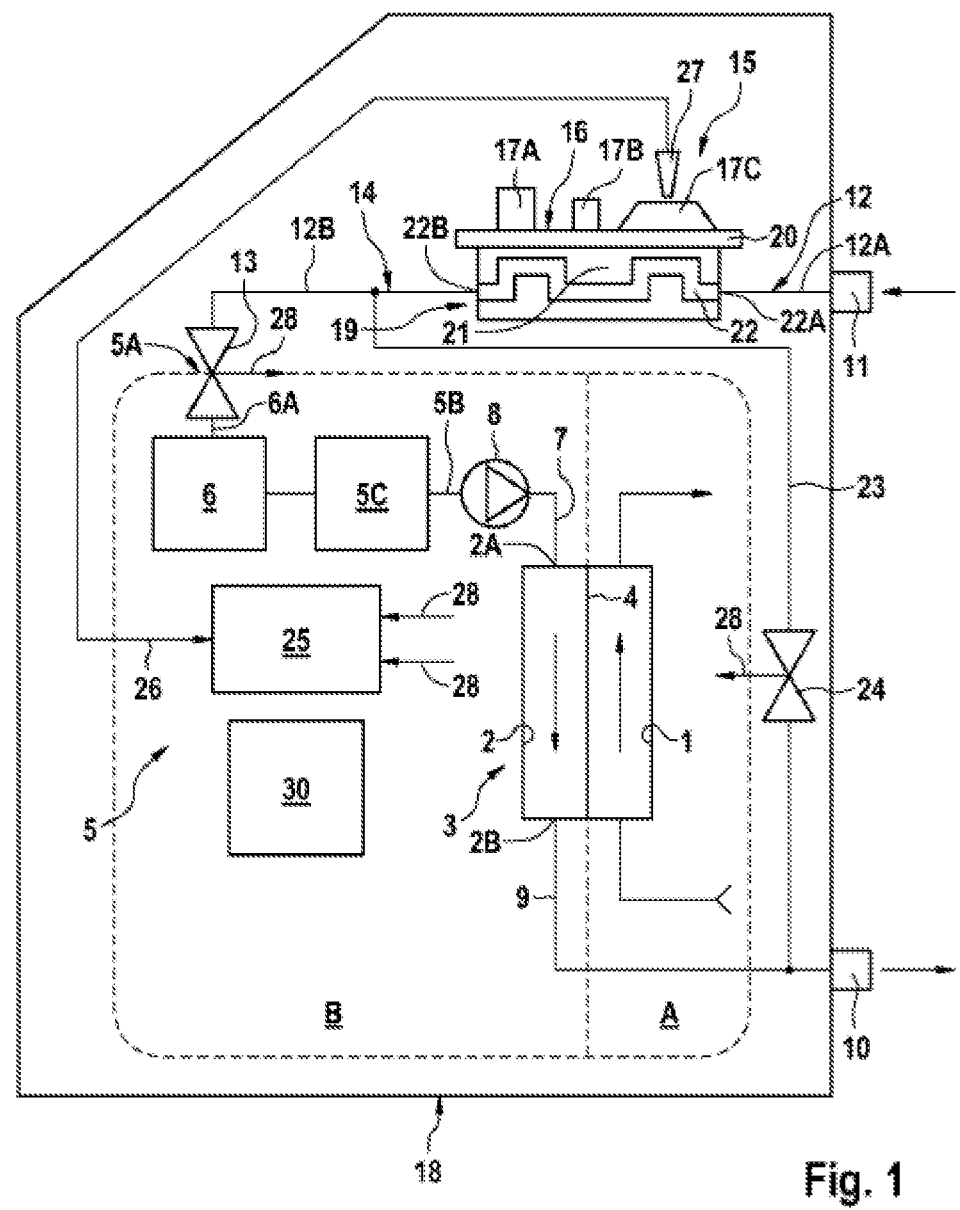

device to dissipate heat from the electrical components. The cooling apparatus (19) has at least one heat sink (21) which can be cooled with a liquid and is in thermal contact with the at least one electrical component (17A), (17B), (17C), wherein the cooling apparatus (19) has at least one inlet (22A) which is fluid-connected to the connection (11) for the inflow of a liquid and at least one outlet (22B) which is fluid-connected to a drain (10), (31).

14 Claims, 4 Drawing Sheets

(52) U.S. Cl.
CPC ..... *H05K 7/20272* (2013.01); *H05K 7/20281* (2013.01); *A61M 2205/3368* (2013.01); *A61M 2205/3606* (2013.01); *A61M 2205/366* (2013.01)

(58) Field of Classification Search
CPC .... A61M 2205/3606; A61M 2205/366; A61M 2205/50; H05K 7/20254; H05K 7/20272; H05K 7/20281
See application file for complete search history.

(56) References Cited

U.S. PATENT DOCUMENTS

2016/0030660 A1    2/2016   Sun et al.
2018/0236156 A1    8/2018   Glaser

OTHER PUBLICATIONS

International Search Report and Written Opinion issued in corresponding International Patent Application No. PCT/EP2018/059207(with English translation of International Search Report) dated Jul. 3, 2018 (16 pages).

DEVICE FOR EXTRACORPOREAL BLOOD TREATMENT AND METHOD FOR OPERATING AN EXTRACORPOREAL BLOOD TREATMENT DEVICE

This application is a National Stage Application of PCT/EP2018/059207, filed Apr. 10, 2018, which claims priority to German Patent Application No. 10 2017 003 508.3, filed Apr. 11, 2017.

The invention relates to a device for extracorporeal blood treatment, comprising a hydraulic system that has a plurality of lines and is intended for providing dialysate for a dialyser or dialysis treatment, the dialysate flowing through the dialyser and/or the dialysate being supplied as a substitute to an extracorporeal blood tube system during treatment, and comprising a control system having at least one electrical component, usually a plurality of electrical components. The invention also relates to a method for operating a device for extracorporeal blood treatment, which device comprises a hydraulic system that has a plurality of lines and is intended for providing dialysate for a dialyser or dialysis treatment, the dialysate flowing through the dialyser and/or the dialysate being supplied as a substituate to an extracorporeal blood tube system during treatment, and which comprises a control system having at least one electrical component, usually a plurality of electrical components, the dialysate being produced using a fluid that is supplied to the device for extracorporeal blood treatment.

During dialysis, the blood to be treated flows in an extracorporeal blood circuit through the blood chamber of a dialyser divided by a semi-permeable membrane into the blood chamber and a dialysate chamber, while dialysate flows through the dialysate chamber of the dialyser. The extracorporeal blood circuit comprises a blood supply line, which leads to the blood chamber, and a blood discharge line, which leads away from the blood chamber. The hydraulic system of the device for extracorporeal blood treatment has a line leading to the dialyser for supplying fresh dialysate and a line leading away from the dialyser for discharging used dialysate into a drain. Pumps are provided for conveying the fluids. All the components of the device for extracorporeal blood treatment are controlled by a control system that comprises a plurality of electrical components. The control system can consist of one or more subassemblies. This description is an example for dialysis. In the context of the present invention, the term dialysis also includes hemofiltration, in which the dialysate is not supplied to the dialysate chamber, but is supplied as a substituate to the blood supply line and/or the blood discharge line, and fluid is removed by means of the dialyser. In the context of the present invention, the term dialysis includes all the combinations of said methods.

The dialysate can be produced in the dialysis machine from permeate (pure water) and one or more concentrates. The dialysis machines have a water connection for supplying the permeate. The dialysate is prepared in the hydraulic system of the machine. However, "bedside stations" are also known and constitute embodiments in which the dialysate is supplied to the dialysis machine from the outside.

When reference is made to "water" or "pure water" in the following, this is also understood to mean dialysate or a rinsing fluid that is supplied to the dialysis machine from the outside or is provided in the dialysis machine. In the context of the present invention, "water" and "pure water" may have the same or a different meaning. A person skilled in the art will know from the technical context whether the water may also be pure water. In case of doubt, the terms ought to be considered synonymous.

Dialysis machines increasingly have a compact design. The reasons for this development are improved transport capability and the need to save space in cramped conditions in clinics or in home dialysis. Another development is that hot-water purification or hot-water disinfection processes have become very common in dialysis machines, and these processes continue to grow in importance. These processes allow, inter alia, the use of chemicals to be reduced. During the hot-water disinfection process, permeate and/or permeate mixed with disinfectant circulates in the hydraulic system at a temperature of greater than 80° C. The terms hot-water purification and hot-water disinfection ought to be considered synonymous in the present description unless a person skilled in the art concludes from the context that one or the other process is meant. In principle, disinfection also has a purifying effect, whereas purification does not necessarily lead to disinfection. It is therefore possible to purify at a significantly lower temperature than it is to disinfect, for example.

Thermal management is becoming increasingly challenging in dialysis machines having a compact design. In particular, the temperature inside the housing of the dialysis machine can increase rapidly during hot-water disinfection. A high temperature inside the housing is necessary or at least helpful for reaching the temperature required for the hot-water disinfection. The air temperature inside the unit can be from 50° C. to 65° C.

The high air temperature poses a problem for the electrical components of the control system, for example power semiconductors or processors. This problem is only exacerbated by the fact that the electronics in compact dialysis units are located in close proximity to the components of the hydraulic system.

Many electrical components are only permitted to reach a temperature of at most 45° C./50° C. Furthermore, the service life of electrical components reduces significantly if certain temperatures are exceeded. Sufficient cooling of the electrical components is therefore necessary. Electrical components are generally cooled using known heat sinks, on which the components are mounted. However, this cooling has been shown to be insufficient at high temperatures inside the housing.

Therefore, the prior art includes dialysis machines having additional fans that are controlled as needed. Although the thermal problem can be solved using the fans, there are, however, disadvantages associated therewith.

First of all, fans lead to additional production costs. It should be considered in this respect that fans only have a limited service life. The intake of dust into the units is also increased using fans, and increased sound levels are also a consequence thereof. Moreover, air cooling has not always been shown to be practicable in countries with very high external temperatures.

The problem addressed by the invention is therefore that of producing a device for extracorporeal blood treatment in which the above-mentioned disadvantages are avoided. The problem addressed by the invention is in particular that of providing a device for extracorporeal blood treatment that operates reliably even at high external temperatures. A further problem addressed by the invention is that of providing a method by means of which a device for extracorporeal blood treatment can be operated without the above-mentioned disadvantages.

This problem is solved according to the invention by the features of the independent claims. The dependent claims relate to preferred embodiments of the invention.

The device for extracorporeal blood treatment according to the invention is a blood treatment device having a central port in order to be able to supply the machine with a fluid, in particular permeate (pure water). The fluid can be used to produce dialysate or for hot-water disinfection. Since the fluid is supplied, a sufficient amount of fluid is available. The temperature of the fluid is largely independent of the room temperature and can, by means of the central supply, be set to a specified value that may also be below a potentially high room temperature.

The device has a cooling apparatus for cooling at least one of the electrical components of the control system, which apparatus uses the fluid, in particular permeate (pure water), supplied centrally to the device in order to conduct heat away from the electrical components. The cooling apparatus has at least one heat sink that can be cooled by a fluid and is in thermal contact with the at least one electrical component, the cooling apparatus having at least one inlet that is in fluid connection with the port for supplying a fluid, and having at least one outlet that is in fluid connection with a drain. The thermal contact is preferably a touching contact or an orientation contact, in which the heat sink for example directly touches a circuit board, or the heat sink is oriented such that the cooling effect thereof is efficiently transferred to the electrical components. This can be achieved by the heat sink being arranged so as to be spaced from the electrical component by less than 30 cm, preferably 20 cm or 10 cm.

Individual, a plurality of or all the thermally loaded electrical components of the device for extracorporeal blood treatment can be cooled by the cooling apparatus. In particular, individual, a plurality of or all the thermally loaded electrical components can be cooled that have a specification stating that they should not be heated above 45° C. or 50° C., or which would be subject to a temperature of above 45° C. or 50° C. or 60° C. during a hot-water disinfection or a hot-water purification process when operating the device without cooling. In this connection, electrical components are understood to be all electric or electronic elements of the control system. The control system is understood to be the entire electronics of the device for extracorporeal blood treatment, i.e. all the electric or electronic elements or components that can also form individual circuits or subassemblies. The cooling apparatus can also comprise a plurality of heat sinks.

It is not essential to the invention how the heat sink, which is in thermal contact with the at least one component and is cooled by the fluid, is designed. It is important, however, that the heat sink is in thermal contact with the fluid so that the heat can be conducted away. The heat sink, which consists of a thermally conductive material, for example aluminium, can be surrounded by the fluid and/or the fluid can flow therethrough. For example, channels can be formed in the heat sink. The fluid can flow in through one or more inlets and flow out through one or more outlets. The fluid can then be ejected. The fluid is directed to a drain, which may be an additional drain or the drain for the used dialysate that is present by default in a dialysis machine.

The at least one heat sink is cooled using the fluid, preferably during an operating mode of the device for extracorporeal blood treatment in which the thermal load is highest. This operating mode may be the hot-water disinfection of the hydraulic system, in which fluid heated to a specified temperature flows through at least some of the lines of the hydraulic system. The invention advantageously makes use of the fact that, in the dialysis machine, the supply path for the central fluid supply with a fluid, in particular permeate, is regularly excluded from the hot-water disinfection circulation. As a result, the cooling apparatus can be connected into the supply path or into a bypass line that is fluidically connected to the supply path and can be connected to the drain. The cooling apparatus can thus be operated independently of the hot-water disinfection process. Such an arrangement in the supply path also results in a situation whereby cooling the electrical component down heats the cooling fluid up, which cooling fluid is subsequently directed, at least in part or completely, into the hydraulic system, where said cooling fluid no longer has to be heated as intensely, whether for a treatment or for a hot-water disinfection. It is thus possible to save energy.

A preferred embodiment of the invention provides for the hydraulic system to have a fluid-preparation apparatus comprising an inlet, the port for supplying a fluid via a supply line being connected to the inlet of the fluid-preparation apparatus. This supply line forms the supply path for the central fluid supply. The fluid can be dialysate, the fluid-preparation apparatus being a dialysate-preparation apparatus.

In this connection, a fluid-preparation apparatus is understood to be all the components of the dialysis machine that are used to prepare a fluid, for example producing, heating or degassing the dialysate. The fluid-preparation apparatus can for example comprise an input chamber for collecting a fluid or a degassing chamber or a heater, etc.

If the fluid-preparation apparatus has an input chamber for collecting a fluid, the inlet of the fluid-preparation apparatus can be an inlet of the input chamber. Consequently, the supply path only comprises the region upstream of the input chamber, and therefore a hot-water disinfection of the hydraulic system can take place irrespective of the supply of fluid to the cooling apparatus in the event of an interruption or adjustment of the supply of fluid into the input chamber. In a particularly preferred embodiment, means for interrupting or adjusting the fluid flow are provided in the supply line.

Different embodiments show different configurations for installing the cooling apparatus in the existing fluid system of the dialysis machine.

In a first embodiment, the supply line has a first portion that connects the port for supplying a fluid to the inlet of the cooling apparatus, and a second portion that connects the outlet of the cooling apparatus to the inlet of the fluid-preparation apparatus. The cooling apparatus is therefore connected into the supply line. During the hot-water disinfection process, the supply of fluid into the hydraulic system can be interrupted such that the fluid only flows to the cooling apparatus. The outlet of the cooling apparatus can be in fluid connection, via a bypass line, with a drain, which may be an additional drain or an existing drain in the dialysis machine. Means, which can be valves or throttles, are provided in the bypass line for interrupting or adjusting the fluid flow. The interruption means can also be pumps or combinations of the various above-mentioned means.

A particularly preferred embodiment provides for the cooling apparatus to have a temperature sensor for measuring the temperature of an electrical component that is in thermal contact with the heat sink, and to have a control unit that actuates the means for interrupting or adjusting the fluid flow in the bypass line such that the temperature is below a specified threshold value. The control unit of the cooling apparatus can also be a component of the central control and arithmetic unit of the device for extracorporeal blood treatment.

In a further embodiment, a first portion of an additional cooling fluid line connects the port for the intake of fluid or the supply line to the inlet of the cooling apparatus, the outlet of the cooling apparatus being in fluid connection, via a second portion of the cooling fluid line, with a drain, which again can be an additional drain or an existing drain in the dialysis machine. Means for interrupting or adjusting the fluid flow are preferably provided in the cooling fluid line. The cooling fluid line therefore constitutes another bypass line. In this embodiment too, adjusting the fluid flow can depend on the temperature of the at least one component.

In a further alternative embodiment, a first portion of a rinsing fluid line branches off from the supply line and leads to the inlet of the cooling apparatus, the outlet of the cooling apparatus being in fluid connection, via a second portion of the rinsing fluid line, with a drain. A rinsing fluid line of this kind may be present in a dialysis machine in order to rinse and/or disinfect the supply path using a fluid that is already present. This line is then used both for rinsing and/or disinfecting the supply path and for supplying the fluid to the cooling apparatus. The rinsing fluid line therefore constitutes another bypass line. The temperature may also be adjusted again here.

Instead of adjusting the temperature of the shut-off members or valves in the lines, the shut-off members or valves can also be time-controlled. For example, the shut-off members or valves can be opened or closed, completely or in part, by the control unit for specified periods of time.

Figure 2:
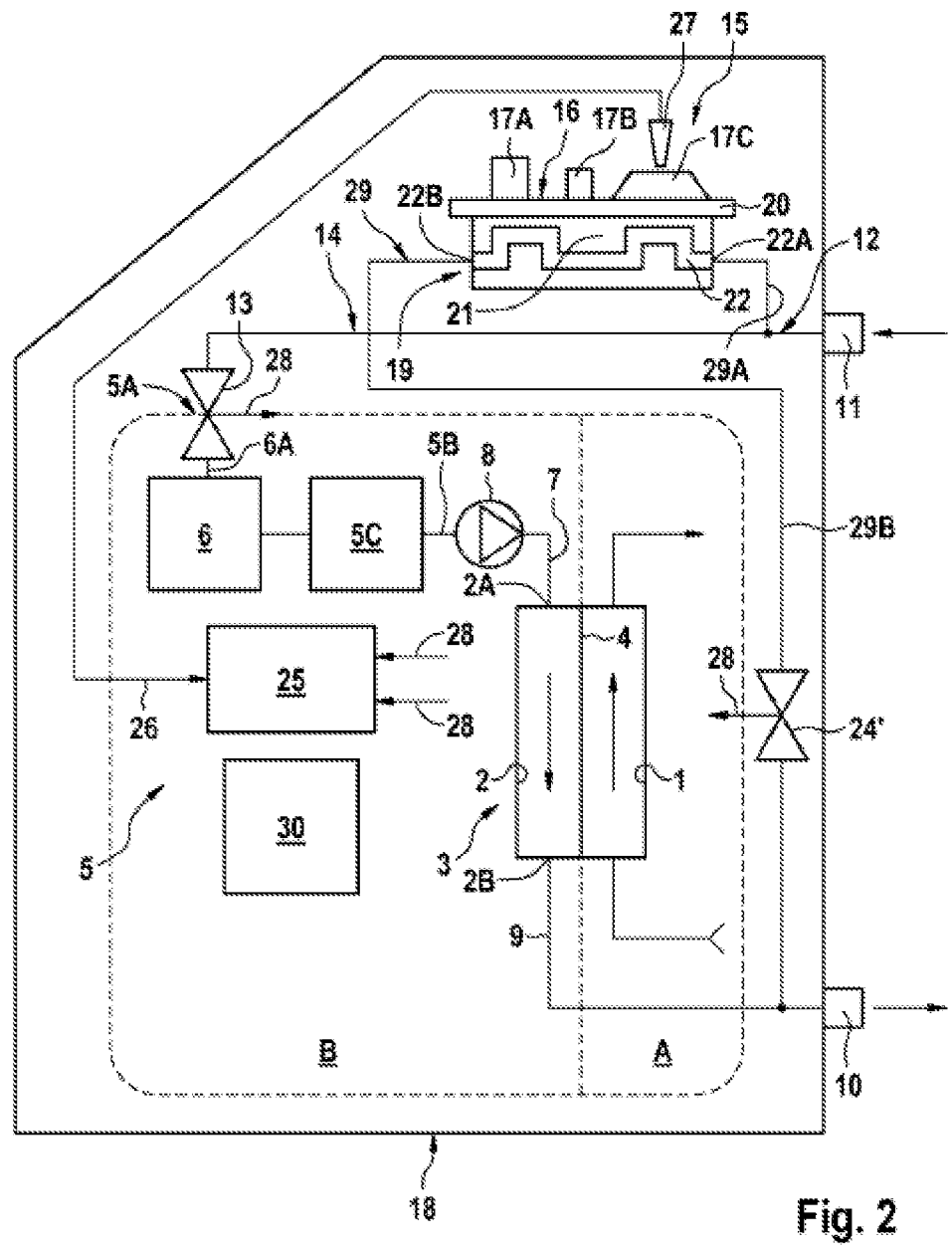
Figure 3:
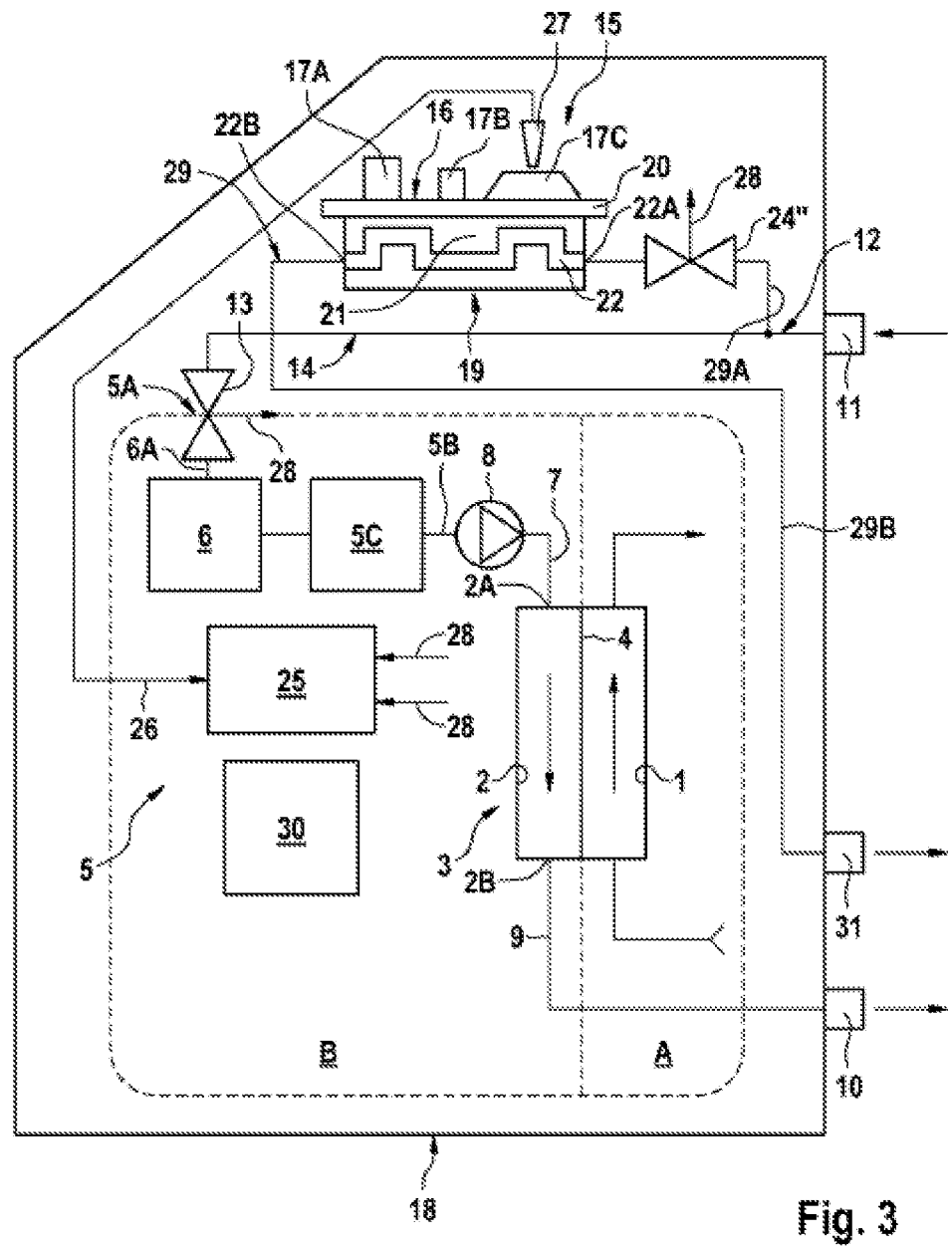
Figure 4:
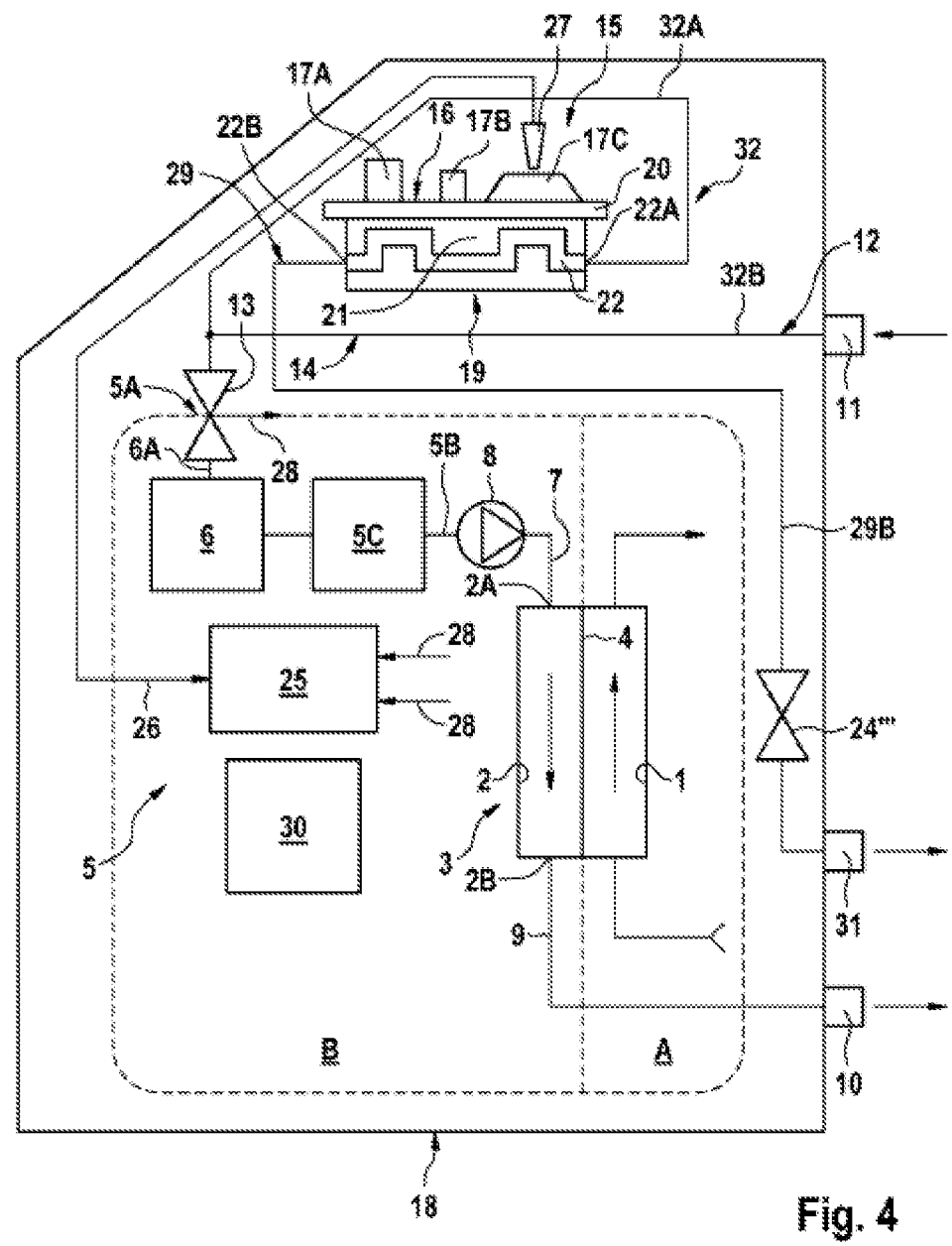

The invention is described in detail below with reference to the drawings, in which:

FIG. 1 is a highly simplified schematic view of a first embodiment of the blood treatment device according to the invention comprising a cooling apparatus, FIG. 2 shows a second embodiment of the blood treatment device according to the invention, FIG. 3 shows a third embodiment of the blood treatment device according to the invention, and FIG. 4 shows a fourth embodiment of the blood treatment device according to the invention.

FIG. 1 is a highly simplified schematic view of an embodiment of the blood treatment device according to the invention. The blood treatment device comprises an extracorporeal blood circuit A (only shown in outline) and a hydraulic system B. The extracorporeal blood circuit A incorporates the blood chamber 1 and the hydraulic system B incorporates the dialysate chamber 2 of a dialyser 3. The blood chamber 1 and the dialysate chamber 2 of the dialyser 3 are separated by a semi-permeable membrane 4. In order to prepare the dialysate, the hydraulic system B has a fluid-preparation apparatus 5, in particular a dialysate-preparation apparatus, that has an inlet 5A for a fluid for producing the dialysate, in particular permeate (pure water), and an outlet 5B. The permeate can be collected in an input chamber 6. The permeate is mixed with one or more concentrates in order to produce the dialysate. The remaining components 5C of the dialysate-preparation apparatus 5 are only shown schematically in FIG. 1. A dialysate supply line 7 leads from the outlet 5B of the dialysate-preparation apparatus 5 to the inlet 2A of the dialysate chamber 2 of the dialyser 3. The dialysate is conveyed by means of a dialysate pump 8. The outlet 2B of the dialysate chamber 2 is connected via a dialysate discharge line 9 to a drain 10 for used dialysate.

This description relates to a phase which involves treatment of a patient. During preparation or follow-up of the treatment, the device does not need to have the components of the extracorporeal blood circuit A and the dialyser 3, or the dialysate supply line 7 can be short-circuited to the dialysate discharge line 9 by bypassing the dialyser 3. The device can also be provided with disinfectant concentrate ports. Concentrated disinfectant can be supplied to the hydraulic system B via the disinfectant concentrate ports and, by being mixed with water that can be supplied to the hydraulic system B via a supply path 14, the desired disinfectant concentration can be made available in the hydraulic system B.

The permeate is supplied to the blood treatment device at a central port 11 that is connected to the inlet 6A of the input chamber 6 of the dialysate-preparation apparatus 5 via a supply line 12. An inlet valve 13 is provided on the inlet 6A of the input chamber 6, and therefore the hydraulic system B can be separated from the supply path 14.

FIG. 1 only shows the components of the hydraulic system B that are essential to the invention. The hydraulic system B may comprise additional components 30, for example a balancing unit.

In addition, the blood treatment device has a control system 15, which can comprise a plurality of circuits having electrical components. FIG. 1 only shows one circuit 16 having a plurality of components 17A, 17B, 17C.

The blood treatment device provides an operating mode for a hot-water disinfection of the hydraulic system B, in which the hydraulic system is rinsed with the fluid that is supplied to the blood treatment device at the central port 11. For this purpose, the fluid, in particular permeate, is heated to a temperature above 80° C. During the hot-water disinfection process, the air temperature within the housing 18 of the blood treatment device increases, which leads to thermal loading of the electrical components 17A, 17B, 17C.

A cooling apparatus 19 is provided for cooling the electrical components 17A, 17B, 17C, which will be described below for one embodiment. The electrical components 17A, 17B, 17C are located on a board 20 that is mounted on a heat sink 21 such that the elements are in thermal contact with the heat sink. The heat sink 21 has one or more channels 22 having an inlet 22A and an outlet 22B such that a fluid can flow through the heat sink in order to conduct heat away from the heat sink. The permeate that is supplied centrally to the machine is used as the cooling fluid for the heat sink.

In the present embodiment, the heat sink 21 is connected into the supply line 12. The supply line 12 comprises a first portion 12A that connects the port 11 to the inlet 22A of the heat sink 21, and a second portion 22B that connects the outlet 22B of the heat sink 21 to the inlet 6A of the input chamber 6. A bypass line 23 leading to the drain 10 branches off from the second portion 12B of the supply line 12. A bypass valve 24 is provided in the bypass line 23.

During the hot-water disinfection process, the inlet valve 13 on the input chamber 6 can remain closed, at least temporarily, such that the hydraulic system B is separated from the supply path 14. The bypass valve 24 in the bypass line 23 is opened so that cold permeate for conducting away heat flows into the heat sink 21. The permeate then flows out into the drain 10.

In an embodiment, the cooling apparatus 19 can have a control unit 25 for controlling the fluid flow, which unit may be a component of the control and arithmetic unit of the blood treatment device, i.e. part of the control system. The control unit 25 is connected, via a measuring line 26, to a temperature sensor 27 that measures the temperature of an electrical component 17C of the electrical circuit 16, and is connected to the inlet valve 13 and the bypass valve 24 via control lines 28. The control unit 25 compares the temperature measured by the temperature sensor 27 with a specified threshold value which is below the permitted operating temperature of the component. If the temperature is above the threshold value, the control unit 25 opens the bypass valve 24 so that permeate flows through the heat sink 21 for conducting away heat. If the temperature is below the threshold value, the control unit 25 closes the bypass valve 24 so that the fluid flow is interrupted. A throttle specifying a certain flow rate can also be provided in the bypass line 23 instead of a valve. The control unit 25 can also adjust the fluid flow into the hydraulic system B by only partly opening and closing the inlet valve 13. The control unit 25 can also control the fluid flow in the supply line 12 in such a way that fluid flows primarily into the hydraulic system B if such a flow is requested by a hydraulic control. If this flow is insufficient for cooling, the control unit 25 can also direct the flow through the bypass line 23, for example by opening the valve 24, as a secondary measure.

In all the embodiments described here, a pump (not shown in the drawings) may be provided in the device, by means of which pump the fluid can be pumped through the bypass line. This pump can be a peristaltic pump or a membrane pump. In this case, the valve 24 can be the peristaltic pump or the membrane pump.

FIG. 2 shows a second embodiment of the blood treatment device, which differs from the first embodiment by the installation of the cooling apparatus 19. The corresponding parts are provided with the same reference signs. In the second embodiment, the heat sink 21 is not connected into the supply line 12. A first portion 29A of an additional cooling fluid line 29 leading to the inlet of the heat sink 21 branches off from the supply line 12. A second portion 29B of the cooling fluid line 29 connects the outlet 22A of the heat sink 21 to the drain 10. A valve 24' is provided in the second portion 29B of the cooling fluid line 29 in order to adjust the coolant flow. The valve 24' in the cooling fluid line 29 can be adjusted by the control unit 25, as with the bypass valve 24 in the bypass line 23 of the first embodiment, depending on the temperature measured by the temperature sensor 27.

FIG. 3 shows a third embodiment of the blood treatment device, which differs from the second embodiment in that the valve 24" for controlling the fluid flow is not arranged in the second portion 29B, but in the first portion 29A of the cooling fluid line. The fluid flow can be adjusted as in the second embodiment. In addition, the third embodiment differs from the second embodiment in that the second portion 29B of the cooling fluid line 29 does not lead to the drain for used dialysate, but to an additional drain 31 for the coolant. However, the second portion 29B of the cooling fluid line 29 may also be connected to the drain 10 for used dialysate in the third embodiment (FIGS. 1 and 2). The third embodiment having the separate outflow 31 for the coolant has the advantage that contamination of the supply path 14 by used dialysate from the drain 10 is excluded.

FIG. 4 shows another alternative embodiment of a blood treatment device which provides for rinsing or disinfection of the supply path 14. For the rinsing or disinfection process, in a blood treatment device of this type a rinsing fluid line 32 is provided that branches off from the supply line 12 upstream of the inlet 5A of the dialysate-preparation apparatus 5, in particular at the end of the supply path 14; for example, said line branches off from the supply line 12 upstream of the inlet valve 13 and preferably close to the inlet valve 13 and leads to a separate drain 31. The heat sink 21 is connected into the rinsing fluid line 32 in the alternative embodiment. The rinsing fluid line 32 comprises a first portion 32A that branches off from the supply line 12 and leads to the inlet 22A of the heat sink 21, and a second portion 32B that connects the outlet 22B of the heat sink 21 to the separate drain 31. The valve 24" for adjusting the coolant flow can be provided in the second portion 32B of the rinsing fluid line 32. In this embodiment, an existing line is thus used to supply the coolant, which line is otherwise used to supply a rinsing fluid. The valves 13 and 24''' can be controlled as in the above embodiments.

The invention claimed is:

1. Device for extracorporeal blood treatment, comprising a hydraulic system that has a plurality of lines and is intended for providing dialysate for a dialysis treatment, and a control system comprising at least one electrical component, the hydraulic system having at least one port for supplying a fluid to the device for extracorporeal blood treatment, wherein
the device for extracorporeal blood treatment has a cooling apparatus for cooling the electrical component or at least one of the electrical components of the control system, which apparatus has at least one heat sink that can be cooled by a fluid and is in thermal contact with at least one electrical component, the cooling apparatus having at least one inlet that is in fluid connection with the port for supplying a fluid, and having at least one outlet that is in fluid connection with a drain and wherein the hydraulic system has a fluid-preparation apparatus having an inlet, the port for supplying a fluid via a fluid line being connected to the inlet of the fluid-preparation apparatus, and a bypass line coming off the supply line, which bypass line is in fluid connection with the drain.

2. Device for extracorporeal blood treatment according to claim 1, wherein the fluid-preparation apparatus has an input chamber for collecting a fluid, the inlet of the fluid-preparation apparatus being an inlet of the input chamber.

3. Device for extracorporeal blood treatment according to claim 1, wherein means for interrupting or adjusting the fluid flow in the supply line are provided downstream of the branch-off of the bypass line from the supply line.

4. Device for extracorporeal blood treatment according to claim 1, wherein the supply line comprises a first portion that connects the port for supplying a fluid to the inlet of the cooling apparatus, and a second portion that connects the outlet of the cooling apparatus to the inlet of the fluid-preparation apparatus.

5. Device for extracorporeal blood treatment according to claim 1, wherein a first portion of the bypass line connects the port for supplying fluid or the supply line to the inlet of the cooling apparatus, the outlet of the cooling apparatus being in fluid connection with a drain via a second portion of the bypass line.

6. Device for extracorporeal blood treatment according to claim 1, wherein means for interrupting or adjusting the fluid flow are provided in the bypass line.

7. Device for extracorporeal blood treatment according to claim 6, wherein the cooling apparatus has a temperature sensor for measuring the temperature of an electrical component that is in thermal contact with the heat sink, and a control unit that actuates the means for interrupting or adjusting the fluid flow in the bypass line such that the temperature is below a specified threshold value.

8. Device for extracorporeal blood treatment according to claim 1, wherein drain is independent of an additional drain for the hydraulic system.

9. Method for operating the device of claim 1 for extracorporeal blood treatment, the dialysate being produced using a fluid that is supplied to the device for extracorporeal blood treatment, wherein, in order to cool at least one component of the control system, said method comprising bringing the component into thermal contact with a heat sink that is cooled using the fluid intended for producing the dialysate.

10. Method according to claim 9, wherein the fluid used to produce the dialysate is permeate.

11. Method for operating the device of claim 1 for extracorporeal blood treatment, wherein the device for extracorporeal blood treatment providing an operating mode for carrying out a hot-water disinfection of the hydraulic system, in which a fluid heated to a specified temperature flows through at least some of the lines of the hydraulic system, said method comprising during the hot-water disinfection operating mode, cooling the heat sink using a fluid that is supplied to the device for extracorporeal blood treatment, while the fluid heated to a specified temperature flows through at least some of the lines of the hydraulic system.

12. Method according to claim 11, wherein the fluid used for the hot-water disinfection is permeate.

13. Method according to claim 9, wherein the temperature of the at least one component is measured, and the supply of the fluid that is supplied to the device for extracorporeal blood treatment is adjusted such that the temperature of the at least one component is below a specified threshold value.

14. Device for extracorporeal blood treatment according to claim 1, wherein the drain is independent of a drain for dialysate during treatment.

* * * * *